United States Patent
Yoon et al.

(10) Patent No.: US 11,492,378 B2
(45) Date of Patent: Nov. 8, 2022

(54) **ANTIBACTERIAL PROTEIN EFAL-2 HAVING BACTERIOLYTIC ABILITY WITH RESPECT TO *ENTEROCOCCUS FAECIUM***

(71) Applicant: Intron Biotechnology, Inc., Gyeonggi-do (KR)

(72) Inventors: Seong Jun Yoon, Seoul (KR); Myung Soo Kang, Seoul (KR); Soo Youn Jun, Seoul (KR); Jong Hyun Kim, Gyeonggi-do (KR); Gi Mo Jung, Seoul (KR); Jee Soo Son, Seoul (KR); Hyoun Rok Paik, Incheon (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 17/100,232

(22) Filed: Nov. 20, 2020

(65) Prior Publication Data

US 2021/0070809 A1    Mar. 11, 2021

Related U.S. Application Data

(62) Division of application No. 16/487,508, filed as application No. PCT/KR2018/000510 on Jan. 11, 2018, now abandoned.

(30) Foreign Application Priority Data

Feb. 22, 2017 (KR) .......................... 10-2017-0023320

(51) Int. Cl.
| | | |
|---|---|---|
| *C07K 14/005* | (2006.01) | |
| *A61P 31/04* | (2006.01) | |
| *C12N 15/70* | (2006.01) | |
| *A61K 38/00* | (2006.01) | |

(52) U.S. Cl.
CPC ............ *C07K 14/005* (2013.01); *A61P 31/04* (2018.01); *C12N 15/70* (2013.01); *A61K 38/00* (2013.01); *C12N 2795/00022* (2013.01)

(58) Field of Classification Search
None
See application file for complete search history.

(56) References Cited

U.S. PATENT DOCUMENTS

2007/0025978 A1   2/2007  Yoong et al.
2014/0336359 A1*  11/2014  Shirvan .................. A61P 31/04
                                                              530/328

FOREIGN PATENT DOCUMENTS

| KR | 101016918 B1 | 2/2011 |
|---|---|---|
| WO | WO-00/69269 A1 | 11/2000 |
| WO | PCT/KR2018/000510 | 1/2018 |
| WO | WO-2018/155813 A2 | 8/2018 |

OTHER PUBLICATIONS

U.S. Appl. No. 16/487,508, filed Aug. 21, 2019, Seong Jun Yoon.
Yoong, et al., "Identification of a Broadly Active Phage Lytic Enzyme with Lethal Activity against Antibiotic-Resistant Enterococcus faecalis and Enterococcus faecium", Journal of Bacteriology, (2004), p. 4808-4812.
International Search Report and Written Opinion dated Nov. 23, 2018 by the International Searching Authority for International Application No. PCT/KR2018/000510, filed on Jan. 11, 2018 and published as WO 2018/155813 on Aug. 30, 2018 (Applicant-Intron Biotechnology, Inc.) (Original—11 Pages/Translated—3 pages).
GenBank: WP_002312833.1 (May 12, 2013).
GenBank: CP014529.1 (Oct. 3, 2016).
Cedars Sinai (downloaded on Jul. 31, 2020 from URL:< https://www.cedars-sinai.org/health-library/diseases-and-conditions/b/bacterial-endocarditis-adult.html>) (Year: 2020).
Medical News Today (downloaded on Jul. 31, 2020 from URL:< https://www.medicalnewstoday.com/ar; (Year: 2020).
StoneSprings Hospital Center (downloaded on Jul. 31, 2020 from URL:< https://stonespringshospital.com/blog/entry/understanding-sepsis>) (Year: 2020).
U.S. Non Final Office Action dated Aug. 24, 2020 by the USPTO for U.S. Appl. No. 16/487,508, filed Aug. 21 2109 12 pages.
Response To Restriction Requirement filed on Jul. 29, 2020 with the USPTO for U.S. Appl. No. 16/487,508, filed Aug. 21 2109 5 pages.
Restriction Election dated Jun. 20, 2020 by the USPTO for U.S. Appl. No. 16/487,508, filed Aug. 21 2109 10 pages.

* cited by examiner

*Primary Examiner* — Sergio Coffa
(74) *Attorney, Agent, or Firm* — Ballard Spahr LLP

(57) ABSTRACT

The present invention relates to an antibacterial protein EFAL-2 derived from bacteriophage Ent-FAP-4 (Accession number: KCTC 12854BP), which has the ability to kill *Enterococcus faecium* and an amino acid sequence represented by SEQ ID NO: 2, a pharmaceutical composition containing the same as an active ingredient, and a method for preventing or treating diseases caused by *Enterococcus faecium* using the pharmaceutical composition.

1 Claim, 4 Drawing Sheets

Specification includes a Sequence Listing.

[FIG. 1]
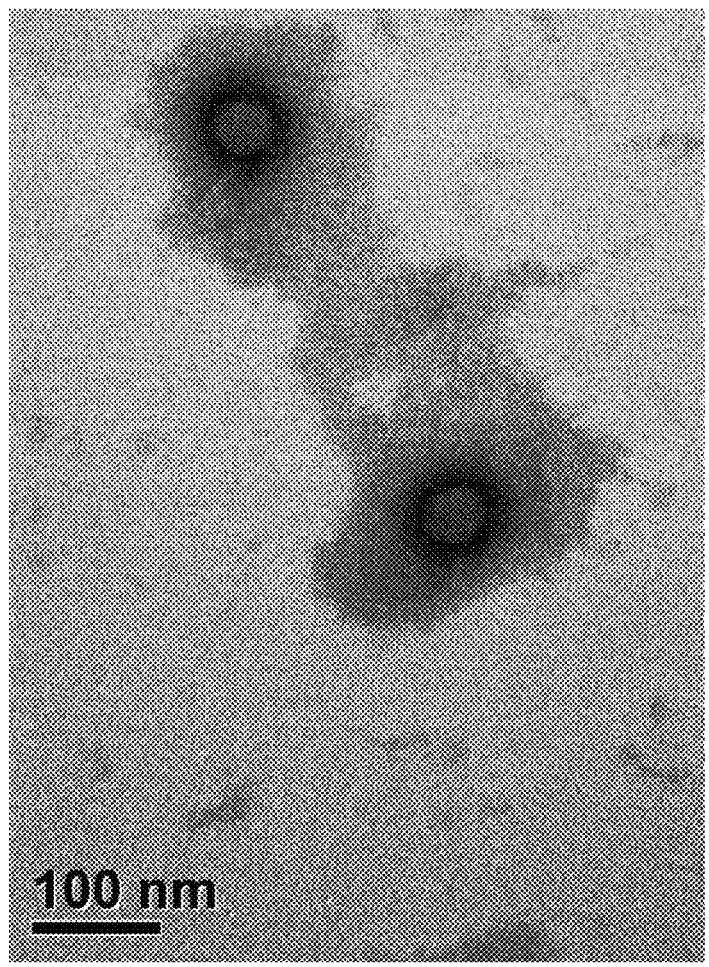

[FIG. 2]
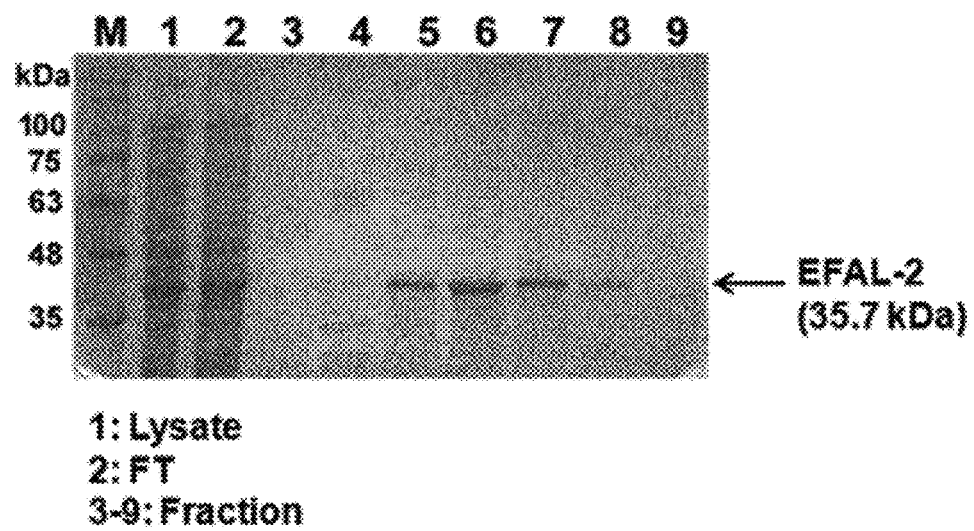
1: Lysate
2: FT
3-9: Fraction

[FIG. 3]
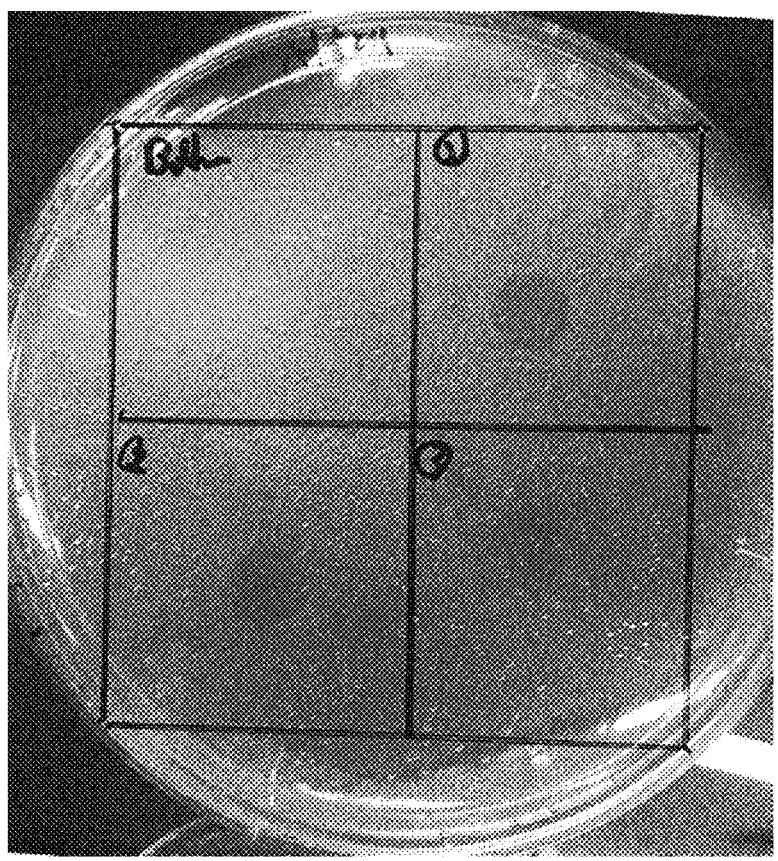

[FIG. 4]
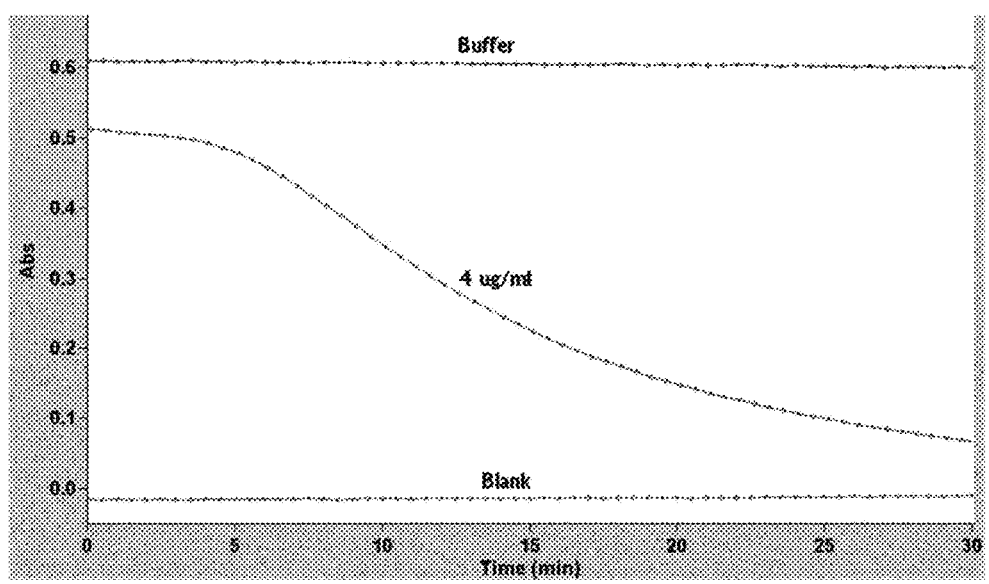

SEQUENCE LISTING

<160> NUMBER OF SEQ ID NOS: 2

<210> SEQ ID NO 1
<211> LENGTH: 975
<212> TYPE: DNA
<213> ORGANISM: Artificial sequence
<220> FEATURE:
<223> OTHER INFORMATION: Using the genetic information of bacteriophage
      Ent-FAP-4 (Accession number: KCTC 12854BP) isolated from nature
<220> FEATURE:
<221> NAME/KEY: gene
<222> LOCATION: (1)..(975)
<223> OTHER INFORMATION: Gene coding antibacterial protein EFAL-2

<400> SEQUENCE: 1

```
atgtacacaa ttgacactag tcagaagtta gcacctaatg aaggctccag ccaagtagct      60
aaccctaact acattatttt gcatgaaacc gctaacccaa acgctggtgg actaaacaat     120
gctaaatata tgaaacgtac atggtataac gcttacacag cttatatcgt tggcgagggt     180
aaagcttacc aagtaggtga agatggttat gtacaatatg gtgctggctc gtatgcaaac     240
gctaacgcac cagtacaaat tgagttagac cacaccacag acaaagcaat gtttcaaaag     300
aactacaaag tatacgttga gttagcacgt gataaagcta aaaaatataa cattcctttg     360
```

```
acgcttgaca cgccttataa tcaacgtggt attaagtcac acttatgggt aactcaaaac    420
atttggggtg accactcaga cccatatggt tacttacaaa gcatgggtat ttctaaacag    480
aaattagctc atgacttagc taacggtttt ggttctgata caaacaatcc agtaccaaac    540
ccaacaccat caaacccaca aacagcacat gacaacgctg tcacaaaatc tgcaccagtt    600
actaacggta attacattgg taaacttgac gtgttcaagg aacaaccaaa aggacaatta    660
cgtattgctg gttggaatgt ggctgtaaat ggtgctgacg cttaccgtta tggttttgtt    720
ttctacatgg acgctaacac tggtaaagaa gtagctcgtt caatgagtaa aggaattgct    780
agaccagatg tttcaaaagc ctatggtttg ccagttacaa acaaatatgg acttgataca    840
actgtgccta tgagtaagtt aaaaggtcac aaaatcattc caatgttcag acgaactaat    900
gacccaagtg aaacactaa aggtggttca catgatgtaa tgttaccaaa catttatatc    960
aatgtaccta ataa                                                      975
```

<210> SEQ ID NO 2
<211> LENGTH: 324
<212> TYPE: PRT
<213> ORGANISM: Artificial sequence
<220> FEATURE:
<223> OTHER INFORMATION: Using the genetic information of bacteriophage
      Ent-FAP-4 (Accession number: KCTC 12854BP) isolated from nature
      and being produced by Escherichia coli TOP10-pBAD-EFAL-2
      (Accession number: KCTC 13177BP)
<220> FEATURE:
<221> NAME/KEY: PEPTIDE
<222> LOCATION: (1)..(324)
<223> OTHER INFORMATION: Antibacterial protein EFAL-2

<400> SEQUENCE: 2

Met Tyr Thr Ile Asp Thr Ser Gln Lys Leu Ala Pro Asn Glu Gly Ser
1               5                   10                  15

Ser Gln Val Ala Asn Pro Asn Tyr Ile Ile Leu His Glu Thr Ala Asn
                20                  25                  30

Pro Asn Ala Gly Gly Leu Asn Asn Ala Lys Tyr Met Lys Arg Thr Trp
            35                  40                  45

Tyr Asn Ala Tyr Thr Ala Tyr Ile Val Gly Glu Gly Lys Ala Tyr Gln
    50                  55                  60

Val Gly Glu Asp Gly Tyr Val Gln Tyr Gly Ala Gly Ser Tyr Ala Asn
65                  70                  75                  80

Ala Asn Ala Pro Val Gln Ile Glu Leu Asp His Thr Thr Asp Lys Ala
                85                  90                  95

Met Phe Gln Lys Asn Tyr Lys Val Tyr Val Glu Leu Ala Arg Asp Lys
            100                 105                 110

Ala Lys Lys Tyr Asn Ile Pro Leu Thr Leu Asp Thr Pro Tyr Asn Gln
        115                 120                 125

Arg Gly Ile Lys Ser His Leu Trp Val Thr Gln Asn Ile Trp Gly Asp
    130                 135                 140

His Ser Asp Pro Tyr Gly Tyr Leu Gln Ser Met Gly Ile Ser Lys Gln
145                 150                 155                 160

Lys Leu Ala His Asp Leu Ala Asn Gly Phe Gly Ser Asp Thr Asn Asn
                165                 170                 175

Pro Val Pro Asn Pro Thr Pro Ser Asn Pro Gln Thr Ala His Asp Asn
            180                 185                 190

Ala Val Thr Lys Ser Ala Pro Val Thr Asn Gly Asn Tyr Ile Gly Lys
        195                 200                 205

-continued

```
Leu Asp Val Phe Lys Glu Gln Pro Lys Gly Gln Leu Arg Ile Ala Gly
    210                 215                 220

Trp Asn Val Ala Val Asn Gly Ala Asp Ala Tyr Arg Tyr Gly Phe Val
225                 230                 235                 240

Phe Tyr Met Asp Ala Asn Thr Gly Lys Glu Val Ala Arg Ser Met Ser
            245                 250                 255

Lys Gly Ile Ala Arg Pro Asp Val Ser Lys Ala Tyr Gly Leu Pro Val
            260                 265                 270

Thr Asn Lys Tyr Gly Leu Asp Thr Thr Val Pro Met Ser Lys Leu Lys
        275                 280                 285

Gly His Lys Ile Ile Pro Met Phe Arg Arg Thr Asn Asp Pro Ser Gly
    290                 295                 300

Asn Thr Lys Gly Gly Ser His Asp Val Met Leu Pro Asn Ile Tyr Ile
305                 310                 315                 320

Asn Val Pro Lys
```

ANTIBACTERIAL PROTEIN EFAL-2 HAVING BACTERIOLYTIC ABILITY WITH RESPECT TO *ENTEROCOCCUS FAECIUM*

CROSS-REFERENCE TO RELATED APPLICATIONS

This application is a Divisional of U.S. application Ser. No. 16/487,508, filed Aug. 21, 2019, which is a U.S. National Phase Application of International Application No. PCT/KR2018/000510, filed Jan. 11, 2018, which claims priority to Korean Application No. 10-2017-0023320, filed Feb. 22, 2017, each of which are hereby incorporated by reference in their entirety.

TECHNICAL FIELD

The present invention relates to an antibacterial protein having bacteriolytic ability against *Enterococcus faecium*, and a method for preventing or treating an *Enterococcus faecium* infection using a composition containing the same as an active ingredient. More particularly, the present invention relates to an antibacterial protein EFAL-2, which has the ability to kill *Enterococcus faecium* and an amino acid sequence represented by SEQ ID NO: 2 and which is developed using the genetic information of bacteriophage Ent-FAP-4 (Accession number: KCTC 12854BP), a pharmaceutical composition containing the antibacterial protein EFAL-2 as an active ingredient, and a method for preventing or treating an *Enterococcus faecium* infection using the pharmaceutical composition.

BACKGROUND ART

*Enterococcus* is facultative anaerobic gram-positive bacteria that are resident in the gastrointestinal tract and the urogenital system. As the *Enterococcus* genus, approximately 19 species including *Enterococcus faecalis*, *Enterococcus faecium*, *Enterococcus durans*, and *Enterococcus casseliflavus* have been reported, among which *Enterococcus faecalis* and *Enterococcus faecium* may be presented as the major species causing actual infection. In the past, infections caused by *Enterococcus faecalis* were very common. However, recently, infections caused by *Enterococcus faecium* have increased relatively.

*Enterococcus* is relatively weakly toxic and thus does not cause diseases in a normal person. However, *Enterococcus* causes various opportunistic infections such as urinary tract infection, wound infection, bacteremia, and endocarditis in elderly people, immunodepressed patients, patients with chronic underlying diseases, or patients that are hospitalized. Further, *Enterococcus* may acquire a virulence factor through gene hybridization from the outside to thus cause infectious diseases. Urinary tract infections are the most frequent infections caused by *Enterococcus*, followed by wound infections. Endocarditis may be presented as other major infections caused by *Enterococcus*, and 5 to 20% of bacterial endocarditis is caused by *Enterococcus*.

Meanwhile, antibiotics such as aminoglycosides, cephalosporins, clindamycin, and semisynthetic penicillin preparations are generally used for *Enterococcus* treatment. However, the observation of resistant bacteria against these antibiotics has been frequently reported. It is known that *Enterococcus* acquires a tolerance to antibiotics by obtaining new DNAs (plasmids, transposons) or using mutations. In particular, when *Enterococcus* that has acquired a tolerance to aminoglycosides causes endocarditis or serious infections, treatment is difficult to succeed because *Enterococcus* cannot be killed. The mortality is reported to reach 67% in cases of bacteremia caused by Vancomycin-Resistance *Enterococcus* (VRE). In 1986, VRE was reported to be resistant to vancomycin for the first time in France. In Korea, VRE was first isolated in 1992. In the United States, since the VRE was first isolated in 1988, data from the NNIS (National Nosocomial Infection Surveillance) showed that 1 to 15% of the isolated *Enterococcus* was VRE between 1990 and 1997 and the ratio of VRE was increased from 25% in 1999 to 28.5% in 2003. In recent years, the emergence of VRE has increased globally in Europe, the United States, Asia including Korea, and Oceania. Accordingly, there is an urgent need to develop drugs that can be used for the prevention or treatment of infections of antibiotic-resistant *Enterococcus*.

Recently, the use of bacteriophages as a countermeasure against bacterial infectious diseases has attracted considerable attention. In particular, the use of bacteriophages is receiving more attention due to excellent antibacterial activity against antibiotic-resistant bacteria. Bacteriophages are very small microorganisms infecting bacteria and are usually simply called "phages". Once a bacteriophage infects bacteria, the bacteriophage proliferates in the inside of the bacterial cell. After proliferation, the progeny of the bacteriophage destroys the bacterial cell wall and escapes from bacteria as the host, suggesting that the bacteriophage has the ability to kill bacteria. The manner in which the bacteriophage infects bacteria is characterized by very high specificity thereof, so that the number of types of bacteriophages infecting a specific bacterium is limited. That is, a certain bacteriophage can infect only a specific bacterium, suggesting that a certain bacteriophage can confer antibacterial effects only upon a specific bacterium.

In order to overcome this relatively narrow range of antibacterial activity, there has been proposed a method of using an antibacterial protein actually acting when bacteriophages exhibit an antibacterial effect against bacteria. The bacteriophage-derived antibacterial protein is named Lysin or Endolysin. In general, the bacteriophage-derived antibacterial protein may provide a broader range of antibacterial activity compared to the bacteriophage as a host thereof.

Bacteriophages or bacteriophage-derived antibacterial proteins are highly specific to bacterial species that act compared to conventional antibiotics. That is, they do not affect bacterial species other than the target bacterial species. The bacterium-specificity of the bacteriophages and bacteriophage-derived antibacterial proteins provides an antibacterial effect (bacteriolytic ability) only for the target bacteria and does not affect commensal bacteria in the environment or in the animal. In general, conventional antibiotics, which have been widely used for bacterial treatment, have simultaneously influenced several kinds of bacteria. This has caused problems such as environmental contamination or disturbance of normal flora of animals. In contrast, the bacteriophages or bacteriophage-derived antibacterial proteins only work for specific bacteria, so that the use of bacteriophages or bacteriophage-derived antibacterial proteins does not cause disturbance of normal flora in the body. Therefore, the use of bacteriophages or bacteriophage-derived antibacterial proteins is very safe compared to the use of antibiotics, and the possibility of side effects caused by use is relatively greatly low.

DISCLOSURE

Technical Problem

Therefore, the present inventors provide an antibacterial protein that can kill *Enterococcus faecium* among Enterococci, which are harmful pathogenic bacteria, using the genetic information of bacteriophages isolated by the present inventors. Further, the present inventors provide a pharmaceutical composition, which contains the developed antibacterial protein as an active ingredient and which is used for preventing or treating an *Enterococcus faecium* infection, and a method which is effectively used for the prevention or treatment of an *Enterococcus faecium* infection using the pharmaceutical composition.

Accordingly, it is an object of the present invention to provide an antibacterial protein EFAL-2 which has the ability to kill *Enterococcus faecium* and an amino acid sequence represented by SEQ ID NO: 2 and which is developed using the genetic information of bacteriophage Ent-FAP-4 (Accession number: KCTC 12854BP).

It is another object of the present invention to provide a method for effectively manufacturing an antibacterial protein EFAL-2 derived from bacteriophage Ent-FAP-4 (Accession number: KCTC 12854BP), which has the ability to kill *Enterococcus faecium* and an amino acid sequence represented by SEQ ID NO: 2.

It is another object of the present invention to provide a pharmaceutical composition for preventing or treating an *Enterococcus faecium* infection, which contains the antibacterial protein EFAL-2 derived from bacteriophage Ent-FAP-4 as an active ingredient.

It is another object of the present invention to provide a method for preventing an *Enterococcus faecium* infection using a pharmaceutical composition which contains an antibacterial protein EFAL-2 derived from bacteriophage Ent-FAP-4 as an active ingredient.

It is another object of the present invention to provide a method for treating an *Enterococcus faecium* infection using a pharmaceutical composition which contains an antibacterial protein EFAL-2 derived from bacteriophage Ent-FAP-4 as an active ingredient.

Technical Solution

In order to accomplish the above objects, the inventors of the present invention endeavored to develop an antibacterial protein EFAL-2, which has an amino acid sequence represented by SEQ ID NO: 2 and excellent bacteriolytic ability to *Enterococcus faecium*, using the genetic information of Siphoviridae bacteriophage Ent-FAP-4 (Accession number: KCTC 12854BP) isolated from nature by the present inventors, which has the ability to kill *Enterococcus faecium*. The present inventors further developed a method for efficiently manufacturing the same, and finally developed a pharmaceutical composition which contains the same as an active ingredient and is used for the purpose of preventing or treating an *Enterococcus faecium* infection, leading to the completion of the present invention.

Therefore, according to an aspect of the present invention, the present invention provides an amino acid sequence of an antibacterial protein EFAL-2 having the bacteriolytic ability to *Enterococcus faecium*. Specifically, the antibacterial protein EFAL-2 has the amino acid sequence represented by SEQ ID NO: 2, and the gene for coding the antibacterial protein EFAL-2 preferably has a base sequence represented by SEQ ID NO: 1. The antibacterial protein EFAL-2 that can kill *Enterococcus faecium* includes 324 amino acids and has a molecular weight of about 35.7 kDa.

It is apparent that the amino acid sequence represented by SEQ ID NO: 2 can be partially modified by a person skilled in the art using known techniques. Such modifications include partial substitutions of amino acid sequences, partial addition of amino acid sequences, and partial deletion of amino acid sequences. However, it is most preferable to apply the amino acid sequence represented by SEQ ID NO: 2 as disclosed in the present invention.

The term "gene" as used in this specification means a gene that encompasses both DNA (gDNA and cDNA) and RNA molecules. The nucleotide, which is a basic constituent unit in a gene, includes not only natural nucleotides but also analogues with modified sugar or base moieties (Chemical Reviews 90: 543-584, 1990).

Further, the present invention provides *Escherichia coli* TOP10-pBAD-EFAL-2 which is transformed *Escherichia coli* strains usable to produce an antibacterial protein EFAL-2 having an amino acid sequence represented by SEQ ID NO: 2. The *Escherichia coli* TOP10-pBAD-EFAL-2 was developed by the present inventors and then deposited at the Korean Collection for Type Cultures on Dec. 27, 2016 (Accession number: KCTC 13177BP).

According to another aspect of the present invention, the present invention provides a pharmaceutical composition which contains an antibacterial protein EFAL-2, having an amino acid sequence represented by SEQ ID NO: 2 and a bacteriolytic ability to *Enterococcus faecium*, as an active ingredient and which can be effectively used for the purpose of preventing an *Enterococcus faecium* infection or treating after the *Enterococcus faecium* infection. Examples of the pharmaceutical composition may include disinfectants or antibiotics, but are not limited thereto.

Contained in the pharmaceutical composition containing the antibacterial protein EFAL-2 as the active ingredient according to the present invention, the antibacterial protein EFAL-2 having the amino acid sequence represented by SEQ ID NO: 2 of the present invention has the bacteriolytic ability to *Enterococcus faecium*. Accordingly, it is effective in the prevention (prevention of infection) or treatment (treatment of infection) of diseases such as urinary tract infection, wound infection, bacteremia, and endocarditis caused by *Enterococcus faecium*. Therefore, the pharmaceutical composition of the present invention may be used for the purpose of preventing or treating diseases caused by *Enterococcus faecium*. The diseases caused by *Enterococcus faecium* in this specification are collectively referred to urinary tract infection, wound infection, bacteremia, and endocarditis.

The *Enterococcus faecium* in this specification is irrespective of whether it is sensitive bacteria to conventional antibiotics or it is resistant bacteria that are resistant to conventional antibiotics. That is, it does not matter whether or not to acquire a tolerance to conventional antibiotics.

In this description, the term "prevention" or "prevent" indicates (i) to block the infections of *Enterococcus faecium*; and (ii) to block the development of diseases caused by an *Enterococcus faecium* infection.

In this description, the term "treatment" or "treat" indicates all actions that (i) suppress the diseases caused by *Enterococcus faecium*; and (ii) relieve the diseases caused by *Enterococcus faecium*.

The pharmaceutically acceptable carrier included in the pharmaceutical composition containing the antibacterial protein EFAL-2 as an active ingredient according to the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The pharmaceutical composition containing the antibacterial protein EFAL-2 as an active ingredient according to the present invention may additionally include lubricants, wetting agents, sweeteners, flavors, emulsifiers, suspending agents, and preservatives, in addition to the above ingredients.

The pharmaceutical composition containing the antibacterial protein EFAL-2 as an active ingredient according to the present invention may be applied or sprayed on a disease site, or may be administered orally or parenterally thereto. The parenteral administration may be performed using intravenous administration, intraperitoneal administration, intramuscular administration, subcutaneous administration, or local administration.

The appropriate application, spray, and dosage of the pharmaceutical composition containing the antibacterial protein EFAL-2 as an active ingredient according to the present invention may depend on factors such as the formulation method, the mode of administration, the age, weight, gender and diseased condition of the subject animal or patient, diet, administration time, administration route, excretion rate, and responsiveness. The ordinarily skilled physician or veterinarian may readily determine and prescribe dosages effective for the desired treatment.

In general, the pharmaceutical composition containing the antibacterial protein EFAL-2 as an active ingredient according to the present invention contains 0.0001 to 10% (w/v or w/w), preferably 0.001 to 1% (w/v or w/w), and most preferably 0.1% (w/v or w/w) of the antibacterial protein EFAL-2 according to the present invention as an active ingredient.

The pharmaceutical composition containing the antibacterial protein EFAL-2 as an active ingredient according to the present invention can be formulated according to a method that can be easily performed by those of ordinary skill in the art to which the present invention pertains using a pharmaceutically acceptable carrier and/or excipient in the form of a unit dose or in a multi-dose container. The formulation may be in the form of a solution, suspension, or emulsion in oil or a water-soluble medium, extract, powder, granule, tablet, or capsule. A dispersing agent or stabilizer may be additionally included.

The pharmaceutical composition containing the antibacterial protein EFAL-2 as an active ingredient according to the present invention may be prepared as disinfectants or antibiotics according to the purpose of use, without limitation thereto. In this specification, the term 'antibiotic' collectively refers to preservatives, bactericides, and antibacterial agents.

For this purpose, antibacterial materials that confer antibacterial activity against other bacterial species may be added to the pharmaceutical composition of the present invention in order to improve the effectiveness thereof. Further, antibacterial proteins (Endolysin) derived from other kinds of bacteriophages, which have antibacterial activity against *Enterococcus faecium*, may be added thereto. The antibacterial proteins derived from bacteriophages may be combined properly so as to maximize antibacterial effects, because the antibacterial activities of the antibacterial proteins against *Enterococcus faecium* may be different from each other in view of the strength or exhibition types thereof.

Advantageous Effects

The method for preventing or treating an *Enterococcus faecium* infection using the pharmaceutical composition containing the antibacterial protein EFAL-2, which is derived from bacteriophage Ent-FAP-4 (Accession number: KCTC 12854BP) and which has an amino acid sequence represented by SEQ ID NO: 2, as an active ingredient according to the present invention may have the advantage of very high specificity for *Enterococcus faecium*, compared to the conventional methods based on antibiotics. This means that the pharmaceutical composition can be used for preventing or treating the *Enterococcus faecium* infection without affecting other commensal bacteria that are useful and has fewer side effects according to the use thereof. In general, when antibiotics are used, commensal bacteria are also damaged, thus entailing various side effects owing to the use thereof.

DESCRIPTION OF DRAWINGS

FIG. 1 is an electron micrograph showing the bacteriophage Ent-FAP-4;

FIG. 2 is an electrophoresis photograph showing the isolation and purification process of an antibacterial protein EFAL-2, in which lane M is a protein size marker, lane 1 is a sample before purification, lane 2 is a chromatography-through solution during purification, and lanes 3 to 9 are purified fractions;

FIG. 3 shows the result of antibacterial activity (bacteriolytic activity) of the antibacterial protein EFAL-2 against *Enterococcus faecium*, in which a transparent portion is generated due to the antibacterial activity (bacteriolytic activity) of the antibacterial protein EFAL-2; and FIG. 4 shows the results of the experiment of a turbidity reduction assay, in which a negative control is a buffer not containing the antibacterial protein EFAL-2, the lateral axis is the time (min), and the longitudinal axis is the absorbance at 600 nm.

MODE FOR INVENTION

Hereinafter, the present invention will be described in more detail with reference to Examples. However, the Examples are merely examples of the present invention, and the scope of the present invention is not limited to the Examples.

Example 1: Isolation of Bacteriophage Capable of Killing *Enterococcus faecium*

Samples were collected from nature to isolate the bacteriophage capable of killing *Enterococcus faecium*. Meanwhile, the *Enterococcus faecium* used for the bacteriophage isolation were isolated and identified as *Enterococcus faecium* by the present inventors in advance.

The isolation procedure of the bacteriophage is described in detail hereinafter. The collected sample was added to a TSB (tryptic soy broth) culture medium (casein digest, 17 g/L; soybean digest, 3 g/L; dextrose, 2.5 g/L; NaCl, 5 g/L; dipotassium phosphate, 2.5 g/L) inoculated with *Enterococcus faecium* at a ratio of 1/1,000, followed by shaking culture at 37° C. for 3 to 4 hrs. Upon completion of the culture, centrifugation was performed at 8,000 rpm for 20 min and a supernatant was recovered. The recovered supernatant was inoculated with *Enterococcus faecium* at a ratio of 1/1,000, followed by shaking culture at 37° C. for 3 to 4 hrs. When the sample contained the bacteriophage, the above procedure was repeated a total of 5 times in order to sufficiently increase the number (titer) of bacteriophages. After repeating the procedure 5 times, the culture broth was subjected to centrifugation at 8,000 rpm for 20 min. After the centrifugation, the recovered supernatant was filtered using a 0.45 μm filter. The obtained filtrate was used in a typical spot assay for examining whether or not a bacteriophage capable of killing *Enterococcus faecium* was included therein.

The spot assay was performed as follows: TSB culture medium was inoculated with *Enterococcus faecium* at a ratio of 1/1,000, followed by shaking culture at 37° C. overnight. 3 ml ($OD_{600}$ of 1.5) of the culture broth of *Enterococcus faecium* prepared above was spread on the TSA (tryptic soy agar: casein digest, 15 g/L; soybean digest, 5 g/L; NaCl, 5 g/L; agar, 15 g/L) plate. The spreading plate left on a clean bench for about 30 min to thus dry the spread solution. After drying, 10 μl of the prepared filtrate was spotted onto the plate that *Enterococcus faecium* was spread. The filtrate was left for about 30 min to dry. After drying, the plate was stationary-cultured at 37° C. for one day, and then examined for the generation of a clear zone at the position at which the filtrate was dropped. In the case of the filtrate generating the clear zone, it is judged that the bacteriophage capable of killing *Enterococcus faecium* is included therein. Through the above examination, the filtrate containing the bacteriophage having the ability to kill *Enterococcus faecium* could be obtained.

The pure bacteriophage was isolated from the filtrate confirmed above to have the bacteriophage capable of killing *Enterococcus faecium*. A conventional plaque assay was used for the isolation of the pure bacteriophage. In detail, a plaque formed in the course of the plaque assay was recovered using a sterilized tip, which was then added to the culture broth of *Enterococcus faecium*, followed by culturing at 37° C. for 4 to 5 hrs. After the culturing, centrifugation was performed at 8,000 rpm for 20 min to obtain a supernatant. The *Enterococcus faecium* culture broth was added to the obtained supernatant at a volume ratio of 1/50, followed by culturing at 37° C. for 4 to 5 hrs. In order to increase the number of bacteriophages, the above procedure was repeated at least 5 times. Then, centrifugation was performed at 8,000 rpm for 20 min to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for the isolation of the pure bacteriophage was generally repeated until the generated plaques became similar to each other in size and morphology. In addition, the final isolation of the pure bacteriophage was confirmed using electron microscopy. Until the isolation of the pure bacteriophage was confirmed using the electron microscopy, the above procedure was repeated. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure isolated bacteriophage is presented in FIG. 1. Based on the morphological characteristics, the novel isolated bacteriophage was confirmed to belong to the Siphoviridae bacteriophage.

The solution containing the pure bacteriophage confirmed above was subjected to the following purification process. The *Enterococcus faecium* culture broth was added to the solution containing the pure bacteriophage at a volume ratio of 1/50 based on the total volume of the bacteriophage solution, followed by further culturing for 4 to 5 hrs. After the culturing, centrifugation was performed at 8,000 rpm for 20 min to obtain a supernatant. This procedure was repeated a total of 5 times to obtain a solution containing a sufficient number of bacteriophages. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hrs. Thereafter, centrifugation was performed at 8,000 rpm for 30 min to obtain the bacteriophage precipitate. The resulting bacteriophage precipitate was suspended in 5 ml of a buffer (10 mM Tris-HCl, 10 mM $MgSO_4$, 0.1% Gelatin, pH 8.0). The resulting material was referred to as a bacteriophage suspension or bacteriophage solution.

As a result, the pure bacteriophage purified above was collected, was named the bacteriophage Ent-FAP-4, and was then deposited at the Korean Collection for Type Cultures on Jun. 23, 2015 (Accession number: KCTC 12854BP).

Example 2: Sequence Analysis of Genome of Bacteriophage Ent-FAP-4 and Obtaining of Sequence of Antibacterial Protein The genome of the bacteriophage Ent-FAP-4 was isolated as follows. The genome was isolated from the bacteriophage suspension obtained using the same method as in Example 1. First, in order to eliminate DNA and RNA of *Enterococcus faecium* included in the suspension, 200 U of each of DNase I and RNase A was added to 10 ml of the bacteriophage suspension and then left at 37° C. for 30 min. After being left for 30 min, in order to stop the DNase I and RNase A activity, 500 μl of 0.5 M ethylenediaminetetraacetic acid (EDTA) was added thereto and then left for 10 min. In addition, the resulting mixture was further left at 65° C. for 10 min, and 100 μl of proteinase K (20 mg/ml) was then added thereto so as to break the outer wall of the bacteriophage, followed by reaction at 37° C. for 20 min. After that, 500 μl of 10% sodium dodecyl sulfate (SDS) was added thereto, followed by reaction at 65° C. for 1 hr. After the reaction for 1 hr, 10 ml of the solution of phenol:chloroform: isoamyl alcohol mixed at a component ratio of 25:24:1 was added to the reaction solution, followed by mixing well. In addition, the resulting mixture was subjected to centrifugation at 13,000 rpm for 15 min to thus separate layers. Among the separated layers, the upper layer was selected, and isopropyl alcohol was added thereto at a volume ratio of 1.5, followed by centrifugation at 13,000 rpm for 10 min to precipitate the genome. After recovering the precipitate, 70% ethanol was added to the precipitate, followed by centrifugation at 13,000 rpm for 10 min to wash the precipitate. The washed precipitate was recovered, vacuum-dried and then dissolved in 100 μl of water. This procedure was repeated to thus obtain a large amount of the genome of the bacteriophage Ent-FAP-4.

Next-generation sequencing analysis was performed using the illumina Mi-Seq instrument at the National Instrumentation Center for Environmental Management in Seoul National University using the obtained genome, thus obtaining the genome sequence information of bacteriophage Ent-FAP-4. From the obtained genome sequence of bacteriophage Ent-FAP-4, the gene sequence corresponding to the antibacterial protein of bacteriophage Ent-FAP-4 could be estimated using NCBI GLIMMER and BLAST. In the estimated gene sequence of the antibacterial protein, the gene sequence (975 bp) of a remaining portion other than the portion corresponding to a signal peptide was used for the development of recombinant production technology for the antibacterial protein derived from bacteriophage Ent-FAP-4. The gene sequence of the antibacterial protein used, except for the portion corresponding to the signal peptide, is represented by SEQ ID NO: 1. For reference, the amino acid sequence (consisting 324 amino acid residues) of the antibacterial protein corresponding to the gene sequence represented by SEQ ID NO: 1 is represented by SEQ ID NO: 2.

As a result of comparing the obtained amino acid sequence with other known bacteriophage-derived antibacterial protein sequences, the antibacterial protein derived from bacteriophage Ent-FAP-4 and having the amino acid sequence represented by SEQ ID NO: 2 was homologous to only autolysin derived from *Enterococcus durans* (WP_016176409.1), which was not bacteriophages, and the degree of homology was very low at 57%. This indicates that the antibacterial protein having the amino acid sequence represented by SEQ ID NO: 2 is a novel antibacterial protein whose function has not been reported so far. This novel antibacterial protein was named EFAL-2.

In addition, based on the fact that different types of antibacterial proteins derived from bacteriophages usually provide different antibacterial properties, it was judged that the antibacterial protein EFAL-2 having the amino acid sequence represented by SEQ ID NO: 2 can provide the antibacterial effect different from that of the other bacteriophage-derived antibacterial proteins reported in the past.

Example 3: Construction of Expression Plasmid of Antibacterial Protein EFAL-2

For the production of an antibacterial protein EFAL-2, an expression plasmid of the antibacterial protein EFAL-2 was constructed. The gene of the antibacterial protein EFAL-2 confirmed in Example 2 was subjected to PCR (polymerase chain reaction) cloning into pBAD-TOPO vector (Invitrogen) using Nco I and Not I restriction enzyme sites. For this purpose, an enterokinase cleavage site present in the pBAD-TOPO vector was removed and the Not I restriction enzyme site was inserted before the cloning, thus constructing a desired substance, and this was then used for the PCR cloning. Further, a site-directed mutagenesis kit (iNtRON Biotechnology, Inc.) was used to adjust a start codon after the cloning, and the expression plasmid of the antibacterial protein EFAL-2 was finally constructed through the above-described procedure. The constructed expression plasmid of the antibacterial protein EFAL-2 was named pBAD-EFAL-2. The nucleotide sequence of pBAD-EFAL-2 was represented by SEQ ID NO: 3. *Escherichia coli* TOP10 was transformed using pBAD-EFAL-2 to construct a production strain of the antibacterial protein EFAL-2, and this production strain was named TOP10-pBAD-EFAL-2. The constructed production strain, TOP10-pBAD-EFAL-2, of the antibacterial protein EFAL-2 was deposited at the Korean Collection for Type Cultures on Dec. 27, 2016 (Accession number: KCTC 13177BP).

Example 4: Preparation of Antibacterial Protein EFAL-2

The preparation of an antibacterial protein EFAL-2 having an amino acid sequence represented by SEQ ID NO: 2 will be described below. In the present Example, *Escherichia coli* TOP10-pBAD-EFAL-2 (Accession number: KCTC 13177BP), which is a transformed *Escherichia coli* strain, deposited by the present inventors at the Korean Collection for Type Cultures on Dec. 27, 2016 (Accession number: KCTC 13177BP) was used as a production strain.

20 mL of an LB culture medium (tryptone, 10 g/L; yeast extract, 5 g/L; sodium chloride, 10 g/L) containing kanamycin at a concentration of 50 µg/ml was inoculated with *Escherichia coli* TOP10-pBAD-EFAL-2 (20 µl added), followed by shaking culture at 37° C. overnight. On the next day, the culture broth, which was cultured overnight in an incubator containing 1 L of the LB culture medium containing kanamycin at a concentration of 50 µg/ml, was added at a volume ratio of 1/100 for $OD_{600}$ (absorbance at 600 nm). Culture was performed under conditions of 200 rpm, 5 L/min aeration, and 37° C. When the cell concentration reached 1.8 to 2.0 on the basis of the absorbance at 600 nm, a culturing temperature was lowered to 16° C., and L-arabinose was added thereto so that a final concentration was 0.2%, thus inducing the expression of the antibacterial protein EFAL-2 having the amino acid sequence represented by SEQ ID NO: 2. After the induction of expression, culture was performed overnight at 16° C. Upon completion of the culture, a cell culture broth was recovered and subjected to centrifugation at 7,000 rpm for 10 min at 4° C., thus recovering a cell precipitate. The recovered cell precipitate was suspended in 20 ml of a 50 mM Tris-hydrochloric acid (Tris-HCl, pH 7.0) buffer per g of the cell precipitate. The prepared cell suspension was subjected to ultrasonication to perform cell disruption. The application condition of the ultrasonication included that a process of applying ultrasonic waves for 3 sec to break the cells and stopping for 3 sec was repeated for a total of 15 min. The application was performed in an ice bath state. After the cell disruption, the disrupted cell solution was subjected to centrifugation at 13,000 rpm for 20 min at 4° C. to recover a supernatant. The obtained supernatant was purified through a typical cation-exchange-chromatography purification process. The purification process will be briefly described as follows. 5 ml of HiTrap™ SP FF (GE Healthcare) was used as a cation-exchange resin. Chromatography was performed after pre-equilibrating the column with buffer A (50 mM Tris-HCl, pH 7.0), a sample was dropped on the column, and 10 CV (column volume) of the buffer A was forced to flow at a flow rate of 5 ml/min, thereby performing washing. After washing, chromatography was performed at a flow rate of 5 ml/min so that a concentration gradient from buffer A to buffer B (50 mM Tris-HCl, 1 M NaCl, pH 7.0) ranged from 0% to 100%. In this process, the elution of the target antibacterial protein EFAL-2 having the amino acid sequence represented by SEQ ID NO: 2 was achieved. The result of analysis of the purified antibacterial protein EFAL-2 using electrophoresis is shown in FIG. 2.

Among the obtained purified fractions, fractions containing the antibacterial protein EFAL-2 at a high concentration (purified fractions corresponding to lane 5, lane 6, and lane 7 in FIG. 2) were collected, and were subjected to dialysis using a buffer (50 mM Tris-HCl, pH 7.0), thus performing medium exchange. Thus, an antibacterial protein EFAL-2 solution having a purity of 90% or more was obtained.

Example 5: Investigation of Antibacterial Activity of Antibacterial Protein EFAL-2 by Spot Assay The present inventors investigated the antibacterial activity of an antibacterial protein EFAL-2 by typical spot assay. Experiments were performed on 5 *Enterococcus faecium* strains, 4 *Enterococcus faecalis* strains, 3 *Staphylococcus aureus* strains, 5 *Salmonella* strains, and 7 *Escherichia coli* strains. The bacteria were distributed from Culture Collection of Antimicrobial-Resistant Microbes (CCARM; No. 429 of First Science Hall in Seoul Women's University, 126 Gongneung 2-dong, Nowon-gu, Seoul) or The American Type Culture Collection (ATCC) in the United States, or were isolated and then identified by the present inventors.

In the experimental method, 2 ml of each bacterial culture broth having an absorbance of about 1 at 600 nm in a TSB culture medium was spread on different plate, dried, and cultured in an incubator at 37° C. for 7 hrs. After confirming that the bacteria were grown, 10 μl of an antibacterial protein EFAL-2 solution (EFAL-2 concentration of 1 mg/ml) was dropped on each plate. A buffer (50 mM Tris-HCl, pH 7.0) containing no EFAL-2 was dropped as a negative control. After spotting, culture was performed in an incubator at 37° C. for about 30 min to 1 hr, and the degree of bacteriolysis of each bacterium was observed. As a result, the antibacterial protein EFAL-2 had an antibacterial activity (bacteriolytic ability) only for *Enterococcus faecium* and no antibacterial activity against other species. The antibacterial activity against *Enterococcus faecium* was confirmed for all *Enterococcus faecium* targets (5 strains) to be tested. Representative experimental results of *Enterococcus faecium* targets are shown in FIG. 3.

From these results, it was confirmed that the antibacterial protein EFAL-2 can provide an excellent bacteriolytic ability against *Enterococcus faecium* and can be effectively used for the prevention or treatment of infectious diseases caused by *Enterococcus faecium*.

Example 6: Investigation of Antibacterial Activity of Antibacterial Protein EFAL-2 by Turbidity Reduction Assay The antibacterial activity of an antibacterial protein EFAL-2 was investigated by turbidity reduction assay using an antibacterial protein EFAL-2 solution. The bacteria to be tested were the same as that of Example 5.

The experimental method of the turbidity reduction assay was as follows. After the bacteria to be tested were suspended in normal saline so that an absorbance was about 0.6 to 0.7 at 600 nm, 0.1 ml of the antibacterial protein EFAL-2 solution (EFAL-2 concentration: 40 μg/ml) was added to 0.9 ml of the suspension (final EFAL-2 concentration: 4 μg/ml), and the absorbance at 600 nm was then measured for 30 min. A buffer (50 mM Tris-HCl, pH 7.0) containing no antibacterial protein EFAL-2 was used as a negative control.

As a result of the experiment, the antibacterial protein EFAL-2 exhibited the bacteriolytic activity only for *Enterococcus faecium*, but did not have the bacteriolytic activity for other bacteria to be tested. Representative experimental results for *Enterococcus faecium* are shown in FIG. 4. It could be confirmed that the antibacterial activity of the antibacterial protein EFAL-2 was very rapidly exhibited in the investigation of the antibacterial activity of the antibacterial protein EFAL-2 by the turbidity reduction assay. It can be said that such rapid exhibition of the antibacterial activity is the characteristic which cannot be provided by any conventional antibiotics.

Example 7: Application Example of Antibacterial Protein EFAL-2 to Prevention of *Enterococcus faecium* Infection To a tube containing 9 ml of a nutrient broth (beef extract, 3 g/L; peptone, 5 g/L), 100 μl of an antimicrobial protein EFAL-2 solution having a concentration of about 1 mg/ml was added. In a control experiment, 100 μl of a nutrient broth was added instead of the antibacterial protein EFAL-2 solution to a tube containing 9 ml of a culture medium having the same composition. Finally, the culture broth of *Enterococcus faecium* was added thereto so that an absorbance was about 0.5 at 600 nm, and the resultant substance was transported to an incubator at 37° C. and then subjected to shaking culture to observe the growth status of *Enterococcus faecium*. As can be observed from the results shown in Table 1, in the case of the tube to which the antibacterial protein EFAL-2 solution was not added, *Enterococcus faecium* was very well grown enough to ensure an absorbance of about 1.4 at 600 nm after 60 min. However, the absorbance at 600 nm was gradually decreased from about 0.1 after 10 min to about 0.05 at 60 min in the case of the tube to which the antibacterial protein EFAL-2 solution was added.

TABLE 1

Growth inhibition of *Enterococcus faecium* ($OD_{600}$ absorbance value)

| Classification | 0 hr after culture | 10 min after culture | 60 min after culture |
|---|---|---|---|
| Control group (not treated) | 0.5 | 0.6 | 1.4 |
| Experimental group (antibacterial protein EFAL-2 solution is added) | 0.5 | 0.1 | 0.05 |

The above results indicate that the antibacterial protein EFAL-2 of the present invention not only inhibits the growth of *Enterococcus faecium* but also has the ability to kill *Enterococcus faecium*. Therefore, it is concluded that the antibacterial protein EFAL-2 can be used as the active ingredient of the composition for preventing an *Enterococcus faecium* infection.

Example 8: Investigation of Treatment Effect of Antibacterial Protein EFAL-2 on *Enterococcus faecium* Infection The treatment effect of an antibacterial protein EFAL-2 on an *Enterococcus faecium* infection was investigated using an antibacterial protein EFAL-2 solution for an infectious animal model.

Five-week-old ICR mice [specific pathogen-free (SPF) grade] having a body weight of about 20 g were used as experimental animals. A total of 20 mice were divided into two groups (10 mice per group), followed by administration of $1 \times 10^8$ cfu of *Enterococcus faecium* per mouse intravenously (i.e., $1 \times 10^8$ cfu/mouse) to thus induce an infection. To one group (treatment group), 0.2 ml of the antibacterial protein EFAL-2 solution (10 mg/ml) was administered at the time of 30 min, 12 hrs, and 24 hrs after the forced-infection. To the other group (control group), only the same volume of buffer (50 mM Tris-HCl, pH 7.0) was administered. The buffer was administered at the time of 30 min, 12 hrs, and 24 hrs after the forced-infection as in the case of administration of the antibacterial protein EFAL-2 solution. For 5 days after the forced-infection, the number of deaths was monitored daily and the presence of specific symptoms was observed twice a day in the morning and afternoon.

As a result, a clear treatment effect was confirmed. The number of deaths is as shown in Table 2 below, and administration of the antibacterial protein EFAL-2 of the present invention provided a remarkable improvement in the survival rate of the infectious animals. Further, no specific reaction was observed in the group to which the antibacterial protein EFAL-2 was administered, compared to various specific reactions, such as erythema of lid margin and the decreased activity, observed in the control group.

TABLE 2

| Group | Number of deaths Days after forced-infection | | | | | Number of deaths/ number of test subjects | Mortality (%) |
|---|---|---|---|---|---|---|---|
| | 1 | 2 | 3 | 4 | 5 | | |
| Control group | 0 | 3 | 2 | 1 | 0 | 6/10 | 60 |
| Treatment group | 0 | 0 | 0 | 0 | 0 | 0/10 | 0 |

From the above results, it is confirmed that the antibacterial protein EFAL-2 of the present invention could be effective in treating an *Enterococcus faecium* infection. This characteristic shows that the pharmaceutical composition containing the antibacterial protein EFAL-2 as an active ingredient can be used for the purpose of treating an *Enterococcus faecium* infection and also can be used for the purpose of treating an *Enterococcus faecium* infection in the same manner as conventional antibiotics.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

[Accession Number]
Name of Depositary Authority: KCTC
Accession number: KCTC 13177BP
Accession date: 20161227

REFERENCE TO SEQUENCE LISTING

The Sequence Listing submitted Nov. 20, 2020 as a text file named "08162_0060U2_Sequence Listing.txt," created on Nov. 19, 2020, and having a size of 5,158 bytes is hereby incorporated by reference pursuant to 37 C.F.R. § 1.52(e)(5).

| I. IDENTIFICATION OF THE MICROORGANISM | |
|---|---|
| Identification reference given by the DEPOSITOR: TOP10-pBAD-EFAL-2 | Accession number given by the INTERNATIONAL DEPOSITARY AUTHORITY: KCTC 13177BP |
| II. SCIENTIFIC DESCRIPTION AND PROPOSED TAXONOMIC DESIGNATION | |
| The microorganism identified under I above was accompanied by: | |
| [ ] a scientific description | |
| [ ] a proposed taxonomic designation | |
| III. RECEIPT AND ACCEPTANCE | |
| This International Depositary Authority accepts the microorganism identified under I above, which was received thereby on Dec. 27, 2016. | |
| V. INTERNATIONAL DEPOSITARY AUTHORITY | |
| Name: Korean Collection for Type Cultures Address: Biological Resource Center in Korea Research Institute of Bioscience & Biotechnology (KRIBB) 181 Ypsin-gil, Jeongup, Jeollabuk-do, Republic of Korea (56212) | Signature(s) of person(s) having power to represent the International Depositary Authority or of authorized official(s): Representative Dec. 28, 2016 |

The invention claimed is:

1. A method for treating endocarditis caused by *Enterococcus faecium*, the method comprising:
administering to a subject a composition comprising an antibacterial protein having bacteriolytic ability against *Enterococcus faecium*, and consisting of the amino acid sequence represented by SEQ ID NO: 2.

* * * * *